United States Patent
Kalvert

(10) Patent No.: US 6,730,049 B2
(45) Date of Patent: May 4, 2004

(54) ADJUSTABLE AND TUNABLE HAND TREMOR STABILIZER

(76) Inventor: Michael A. Kalvert, 365 S. Main St., New City, NY (US) 10956

( * ) Notice: Subject to any disclaimer, the term of this patent is extended or adjusted under 35 U.S.C. 154(b) by 61 days.

(21) Appl. No.: 10/176,579

(22) Filed: Jun. 24, 2002

(65) Prior Publication Data

US 2003/0236475 A1 Dec. 25, 2003

(51) Int. Cl.[7] .............................. A61H 1/00; A61H 3/00; A61B 5/11
(52) U.S. Cl. ............................... 601/5; 601/40; 601/72; 601/87; 600/545; 602/21
(58) Field of Search ................................. 601/5, 40, 46, 601/70, 80, 72, 74; 602/5, 21; 2/17; 248/118.1, 444; 401/6

(56) References Cited

U.S. PATENT DOCUMENTS

| | | | |
|---|---|---|---|
| 818,618 A | * | 4/1906 | Fraley .......................... 601/74 |
| 3,640,273 A | | 2/1972 | Ray |
| 4,511,272 A | * | 4/1985 | Brown et al. ................... 401/6 |
| 5,058,571 A | | 10/1991 | Hall |
| 5,573,011 A | | 11/1996 | Felsing |
| 5,772,620 A | | 6/1998 | Szlema et al. |
| 6,328,706 B1 | | 12/2001 | Yattavong |
| 2003/0006357 A1 | * | 1/2003 | Kaiser et al. ................ 248/550 |

* cited by examiner

Primary Examiner—Dahton D. DeMille
(74) Attorney, Agent, or Firm—Greenblum & Bernstein, P.L.C.

(57) ABSTRACT

A tunable and adjustable device for stabilizing tremors includes a rigid splint for receiving a patient's hand, wrist and forearm, and at least one gyroscope removably and rigidly attachable to said splint and positionable for countereffecting the tremors. Also, a method for tuning and adjusting the device is provided which includes assessing the dynamic characteristics of the patient's tremors, assessing at least one activity the patient intends to perform with his/her hand, wrist, and arm which is subject to tremors, attaching the splint to the patient's hand, wrist, and arm that he/she intends to use for the at least one activity, and attaching and positioning the at least one gyroscope to the splint at least one location which countereffects the patient's tremors.

38 Claims, 14 Drawing Sheets

ADJUSTABLE AND TUNABLE HAND TREMOR STABILIZER

BACKGROUND OF THE INVENTION

1. Field of the Invention

The present invention relates to a medical device intended to be worn by a person suffering from severe debilitating dyskinesia (shaking, tremors). In particular, the present invention is a hand tremor stabilizer which utilizes a gyroscope to counteract unwanted and uncontrollable movements that a person's arms are subject to due to dyskinesia.

2. Discussion of Background Information

There are many individuals who are unable to manage many of the routines of daily living due to the fact that their arms shake uncontrollably. These men and women suffer from a variety of ailments that have a common symptom, severe debilitating dyskinesia (shaking, tremors). Individuals with this problem do not have enough stability and control of their hands to allow them to perform seemingly simple tasks, such as: holding a glass of water without spilling it, eating without the embarrassment of bringing a fork to their mouth while dropping the food, holding and reading a newspaper without it shaking uncontrollably, or signing one's own name.

Currently, there is a known device that has been designed to prevent uncontrollable tremors, i.e., U.S. Pat. No. 5,058,571, which provides a gyroscope that is held against the backside of the human hand by a VELCRO strap to reduce or eliminate the effect of tremors. The gyroscope is driven by an electric motor energized by batteries. The batteries are mounted near the periphery of the gyroscope to enhance the gyroscopic action. In a modified form of the known device, the motor is not mounted on the backside of the hand but is a separate unit to which the gyroscope can be readily coupled and uncoupled when required.

However, U.S. Pat. No. 5,058,571 has several major disadvantages. In particular, the aforementioned device is only capable of canceling out unwanted movement in one planar direction since the gyroscope configuration disclosed is a one flywheel or one dimensional countereffective gyroscope.

To understand the drawbacks of the aforementioned device, it is first essential to understand some basics about gyroscopes and their countereffect to any applied force, otherwise known as precession.

When a gyroscope is spinning it contains stored energy. Under Newton's first law of motion, any body will continue in its state of motion until outside forces change it, whether the body is still or traveling. For every action upon a spinning gyroscope, there is an equal, yet 90 degree reaction to the force applied to the gyroscope. Thus, if the gyroscope is moved, the gyroscope will compensate for this movement. A one flywheel gyroscope is only capable of countereffecting a force vector about one axis or in one plane. A two flywheel gyroscope is capable of countereffecting forces in two planes or two dimensions. A three flywheel gyroscope is capable of countereffecting force in all three dimensions.

Since a gyroscope is an instrument that resists change in the direction in which it is traveling, in spite of external forces which may be attempting to change its course, the gyroscope may be used to dampen and eliminate any outside forces that might be directed toward an object. For purposes of this application, a tremor of the hand, wrist, and arm can be considered such an external force that keeps the same from moving in its planned course. Thus, a gyroscope can be used to stabilize the dyskinesia (tremors) of the hand.

With respect to the handheld gyroscopic device disclosed in U.S. Pat. No. 5,058,571, when the gyroscope is rotating, the gyroscope is only capable of canceling unwanted motion from the arm with respect to one planar direction. As a result, the direction of the force component which the tremor is canceled out depends on the spinning rotation of the gyroscope (i.e. clockwise or counterclockwise). A drawback to the one flywheel approach is that tremors are rarely one dimensional in nature with respect to arm movement. Rather, the arm typically flails in unpredictable motion about one, two, or three axes. Since the aforementioned handheld gyroscope is only a one flywheel design, tremors in the second and third planes are not countereffected.

U.S. Pat. No. 5,058,571 has another major disadvantage in that the placement of the gyroscope is permanently fixed in one position on the device (i.e. above the hand of the user). Because the gyroscope cannot be moved, the cancellation effect of the unwanted tremor force is limited to the area of the user's hand. Since tremors are the result of the larger forearm muscles, as well as the smaller intrinsic muscles of the hand, positioning the gyroscope on the top of the hand is not the most effective position because the countereffect of the gyroscope is truly misfocused on the main source of tremors, i.e., the larger forearm muscles.

Furthermore, the positioning of the gyroscope on the top of the hand may not be ergonomically feasible depending on the activity sought to be performed by the user utilizing the aforementioned device. Also, it would be more desirable to provide a mounting system for the gyroscope which addresses and stabilizes not only the hand area, but also the forearm area of the user.

What is needed is a hand tremor stabilizer which is capable of being adjusted and tuned to a higher degree of fidelity according to the user's needs. For instance, if the user suffers from serious tremors which move his/her hand violently in different directions, a two flywheel gyroscope is preferable over a one flywheel design.

Furthermore, adjustability and tunability is needed with respect to the placement of the gyroscope on the hand, wrist and arm. Each person's tremors are different. As a result, the best way to countereffect the uncontrollable shaking of each person, is to find the best position for the gyroscope for each person's individual tremor characteristics.

SUMMARY OF THE INVENTION

The present invention removes the aforementioned disadvantages by providing a hand tremor stabilizer which is adjustable. In particular, the present invention discloses numerous embodiments which allow a plurality of gyroscopes to be mounted in numerous positions proximate the patient's arm, wrist, and arm area. This feature provides for enhanced ergonomic characteristics. For instance, a patient which may require stabilization of his/her arm while writing on a desk, most likely will prefer a hand tremor stabilizer configuration in which the gyroscope is mounted on the top of the forearm ("dorsal perspective") so that the gyroscope does not interfere with the writing surface. However, a person holding a pistol may prefer a hand tremor stabilizer in which the gyroscope is mounted underneath or on a side of the arm.

Furthermore, an advantage of the present invention is that it is tunable. Each patient's tremors are unique to that individual. Some patients may have violent tremors, while other patients perhaps only have mild shaking. Since the countereffect or stabilization force of a gyroscope is dependent on the number of flywheels the gyroscope has, this characteristic may be utilized to the patient's advantage. For instance, if a patient's tremors are only one dimensional in nature (or only in one plane), then only a one flywheel gyroscope needs to be used since all that is required are countereffective force in the same plane. Furthermore, if the patient's tremors are so predictable that it is known precisely in which direction the tremors will project the patient's arm towards, the gyroscope can be operated to spin in a specific direction to induce panning of the person's arm in a direction opposite to that of the predictable tremors.

However, if a patient's tremors occur over two or three planes, then the application of a two or three flywheel gyroscope or double gyroscope configuration is preferred since these configurations can cancel out forces in all three planes. In this circumstance, the patient's tremors can be analyzed and it can be determined about which axes the tremors most likely will occur. If the patient's tremors cause the patient's arm to pitch up and down, while concurrently the patient's arm rolls (about an axis along the length of his/her arm), then a specific gyroscope, such as a two flywheel gyroscope can be utilized to specifically counteract forces with respect to pitch and yaw.

Another advantage of the present invention is that several embodiments are provided which allow the patient the freedom to choose from what aspect his/her arm is to be supported, such as from the "volar" aspect or "dorsal", or even as a complete clamshell design.

According to an aspect of the present invention, a tunable and adjustable device for stabilizing tremors is provided, including a rigid splint for receiving a patient's hand, wrist and forearm, and at least one gyroscope removably and rigidly attachable to the splint and positionable for countereffecting the tremors. According to another aspect of the present invention, the device includes at least one mounting band for securing the splint to the patient's hand, wrist, and forearm. According to still a further aspect of the present invention, the device includes at least one rigid mounting member attached to the splint, the at least one mounting member having at least one of receiving sockets or threaded holes for receiving a gyroscope mounting fitting.

Other aspects of the present invention include the at least one mounting member attached to one of a bottom, top, and side of the splint. In another aspect of the present invention, the at least one mounting member is attached to the splint in a transverse orientation with respect to a longitudinal length of said splint. Additionally, other aspects of the present invention include at least one mounting member having a plurality of mounting members attached to the splint in a transverse orientation with respect to the longitudinal length of the splint.

In another aspect of the present invention, the at least one mounting member is attached in a longitudinal orientation with respect to a longitudinal length of the splint. According to another aspect of the present invention, the at least one mounting member includes a plurality of the mounting members attached to the splint in a longitudinal orientation with respect to the longitudinal length of the splint. According to still a further aspect of the present invention, the device further includes a rigid plate attached to the splint, the rigid plate having a plurality of receiving sockets or threaded holes for receiving a gyroscope mounting fitting, the receiving sockets or threaded holes being positioned in a matrix to provide multiple mounting positions in both a transverse and longitudinal orientation with respect to a longitudinal length of the splint.

In yet another aspect of the invention, the splint has vertical sidewalls and at least one rigid mounting member attached to each sidewall, the mounting member having at least one receiving socket or threaded hole for receiving a gyroscope mounting fitting. Other aspects of the present invention include the splint being structured to be attached to a dorsal portion of the patient's hand, wrist and forearm. According to another aspect of the present invention, the device includes a plurality of mounting members attached to the splint in a longitudinal orientation with respect to the longitudinal length of the splint, said mounting members each having a plurality of receiving sockets or threaded holes for receiving a gyroscope mounting fitting. According to another aspect of the present invention, the device further includes a power supply for providing power to the at least one gyroscope. According to a further aspect of the present invention, the power supply includes a battery powerpack connected to the gyroscope by a power cord.

According to still a further aspect of the present invention the at least one gyroscope resists motion in at least one of one, two, and three directional planes. According to still a further aspect of the present invention, the at least one gyroscope resists motion in at least one of about an x-axis, y-axis, and z-axis. Additionally, other aspects of the invention include the at least one gyroscope having at least one of one, two, and three flywheels for countereffecting tremors. In yet another aspect of the present invention, the splint includes a pair of splints configured in a clamshell orientation.

Furthermore, the present invention includes an articulated member connecting the at least one gyroscope to the at least one rigid mounting member. In another aspect of the present invention, the articulated member is capable of being adjusted and positioned by at least one of swiveling, telescoping, and rotating about a hinge, before the position of the articulated member is rigidly secured such that the at least one gyroscope is rigidly supported to the splint.

According to another aspect of the present invention, a method for tuning and adjusting a device for stabilizing tremors is provided. The device includes a rigid splint for receiving a patient's hand, wrist and arm and at least one gyroscope removably and rigidly attached to the splint for countereffecting the tremors. The method includes attaching the splint to the patient's hand, wrist, and arm that he/she intends to use for the at least one activity, and attaching and positioning the at least one gyroscope to the splint at least one location which countereffects the patient's tremors.

According to another aspect of the present invention the attaching and positioning is based upon input from the dynamic characteristics of the patient's tremors and the at least one activity the patient intends to perform with his/her hand, wrist, and arm which is subject to tremors. In another aspect of the present invention, the method also includes operating the at least one gyroscope to countereffect the patient's tremors while the patient performs the at least one activity with his/her hand, wrist, and arm which is subject to tremors. According to a further aspect of the present invention, the attaching and positioning includes mounting the at least one gyroscope to the splint so that the splint and at least one gyroscope are balanced as an entire unit.

According to still a further aspect of the present invention, the attaching and positioning includes mounting the at least one gyroscope to the splint in an out of balance position to induce at least one of a pulling, tipping, and rolling force in a desired direction. In another aspect of the present invention, the attaching and positioning includes orienting the at least one gyroscope such that tremors that at least one of pitch about an x-axis, yaw about a y-axis, and roll about a z-axis are countereffected. Other aspects of the present invention include wherein the attaching and positioning includes mounting the at least one gyroscope such that tremors are countereffected in at least one of one, two, and three planar directions.

Further aspects of the present invention include determining a rotational direction of at least one flywheel in said at least one gyroscope, based upon input from the dynamic characteristics of the patient's tremors and the at least one activity the patient to perform with his/her hand, wrist, and arm which is subject to tremors, such that the patient's tremors are countereffected as a result of the rotational direction of the at least one flywheel in the at least one gyroscope. According to other aspects of the present invention, the method includes determining a rotational direction of at least one flywheel in the at least one gyroscope, based upon input from the dynamic characteristics of the patient's tremors and the at least one activity the patient intends to perform with his/her hand, wrist, and arm which is subject to tremors, such that the patient's hand, wrist, and arm are pulled or panned in a direction opposing the patient's tremors, as a result of the rotational direction of the at least one flywheel in the at least one gyroscope.

According to another aspect of the present invention, a method is provided for tuning and adjusting a device for stabilizing tremors. The device includes a rigid splint for receiving a patient's hand, wrist and arm and at least one gyroscope removably and rigidly attached to the splint for countereffecting the tremors. The method includes assessing the dynamic characteristics of the patient's tremors, assessing at least one activity the patient intends to perform with his/her hand, wrist, and arm which is subject to tremors, attaching the splint to the patient's hand, wrist, and arm that he/she intends to use for the at least one activity, attaching the at least one gyroscope to the splint at a position which countereffects the patient's tremors based upon input from the dynamic characteristics of the patient's tremors and the at least one activity the patient intends to perform with his/her hand, wrist, and arm which is subject to tremors, and operating the at least one gyroscope to countereffect the patient's tremors while the patient performs the at least one activity with his/her hand, wrist, and arm which is subject to tremors.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, with reference to the noted plurality of drawings by way of non-limiting examples of exemplary embodiments of the present invention, in which like reference numerals represent similar parts throughout the several views of the drawings, and wherein.

DETAILED DESCRIPTION OF AN EMBODIMENT

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
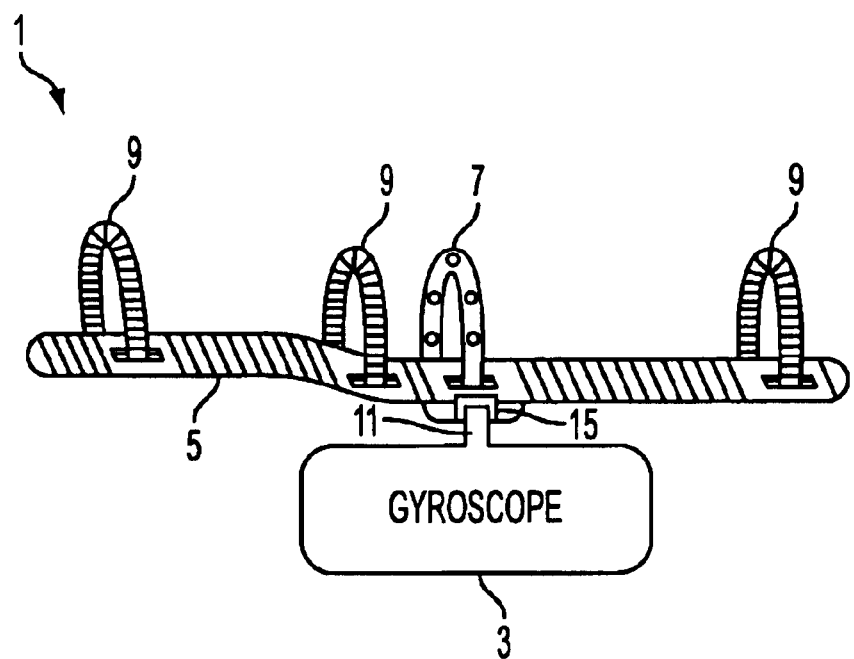
FIG. 1 illustrates a cross-sectional side view of an embodiment of a hand tremor stabilizer with an attached gyroscope which is transversely adjustable.

FIG. 1 illustrates a cross-sectional side view of a first embodiment of a hand tremor stabilizer 1 with an attached gyroscope 3 which is transversely adjustable with respect to the length of the arm. A rigid splint 5 is the primary structure of the device. The splint 5 is capable of stabilizing the entire hand, wrist and forearm region of the patient. In particular, a rigid splint 5 may be utilized to join these three areas of the users body into essentially one stable and rigid structure, except for the free movement of the fingers and thumb.

The splint 5 may be made from a variety of materials already known in the art. For instance, the splint may be manufactured from sturdy, yet lightweight materials, such as aluminum, titanium, plastics or lightweight composites such as epoxy or fiberglass. Furthermore, the splint may be constructed from a variety of designs and shapes already known in the art. It should be noted that the splints disclosed in this application are merely exemplary of a many splint designs that may be utilized as the hand, wrist, and arm supporting member of the present invention.

In the embodiment shown in FIG. 1, the gyroscope 3 is attached to the bottom surface of the splint 5. Detailed specifications on the gyroscope 3 will be provided in greater detail later in the specification. The gyroscope 3 is attached to the bottom side or "volar" (palm) aspect of the splint 5 by using a receiving socket or threaded hole 15 on the splint 5 which is similar to the socket or threaded hole on the bottom of a camera that receives a tripod connection. The patient's hand, wrist, and forearm are attached and fixed to splint 5 using a primary mounting band 7, preferably mounted near the gyroscope attachment point. Also, VELCRO secondary mounting strips 9 are provided for securing the splint 5 to the patient's hand, wrist, and forearm. The splint 5 may also be attached to the patient using other known techniques, such as elastic bands, adjustable belts, straps or any splint fastening technique known in the art.

Figure 2:
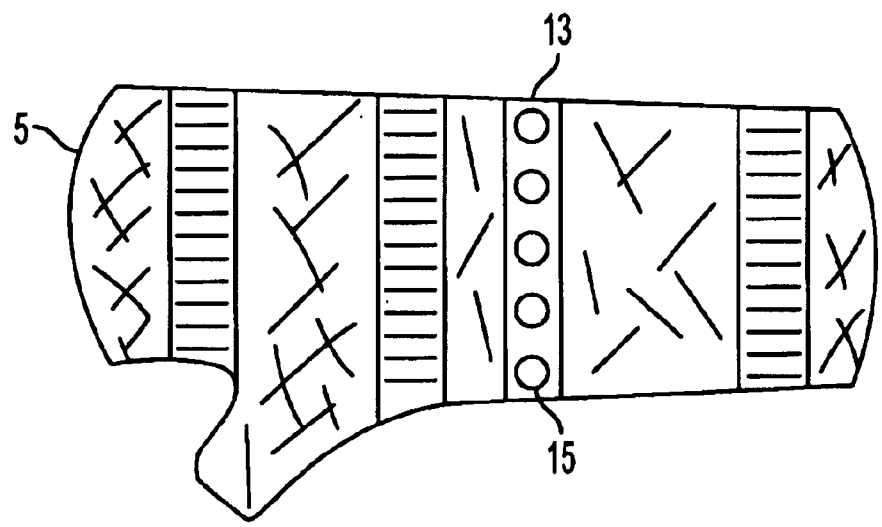
FIG. 2 is a bottom view of the embodiment from FIG. 1, the illustrated embodiment having a transversely configured rigid mounting member mounted to a splint.

FIG. 2 is a bottom view of the embodiment from FIG. 1, which illustrates a transversely configured rigid mounting member 13 attached to the splint 5. The transversely attached rigid mounting member 13 has multiple mounting sockets or threaded holes 15, strong enough to support the gyroscope 3. Also, the transversely attached rigid mounting member 13 may be positioned anywhere along the longitudinal length of the splint 5 (not illustrated) or multiple transversely attached mounting members 13 may be attached to the splint 5, such that the mounting members 13 are spaced apart from each other in a parallel configuration (not illustrated).

Figure 3:
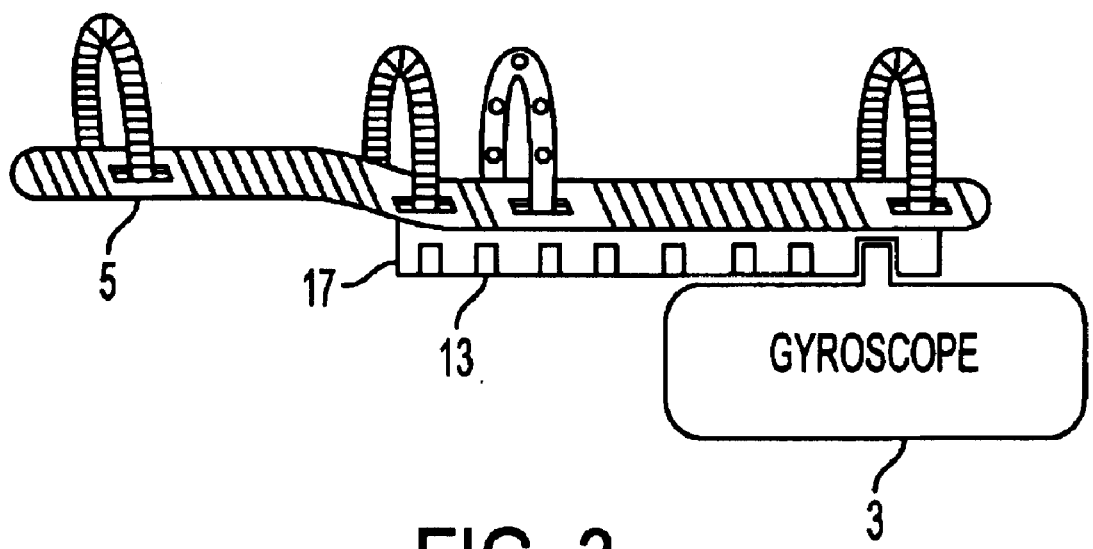
FIG. 3 illustrates a cross-sectional side view of a second embodiment of the hand tremor stabilizer with an attached gyroscope which is longitudinally adjustable.

FIG. 3 illustrates a cross-sectional side view of a second embodiment of the hand tremor stabilizer 1 with an attached gyroscope 3 which is longitudinally adjustable. This alternative embodiment is essentially the same as the embodiment disclosed in FIG. 1 and FIG. 2, however, the transversely attached rigid mounting member 13 is replaced with a longitudinally attached rigid mounting member 17 having multiple mounting sockets or threaded holes 15.

Figure 4:
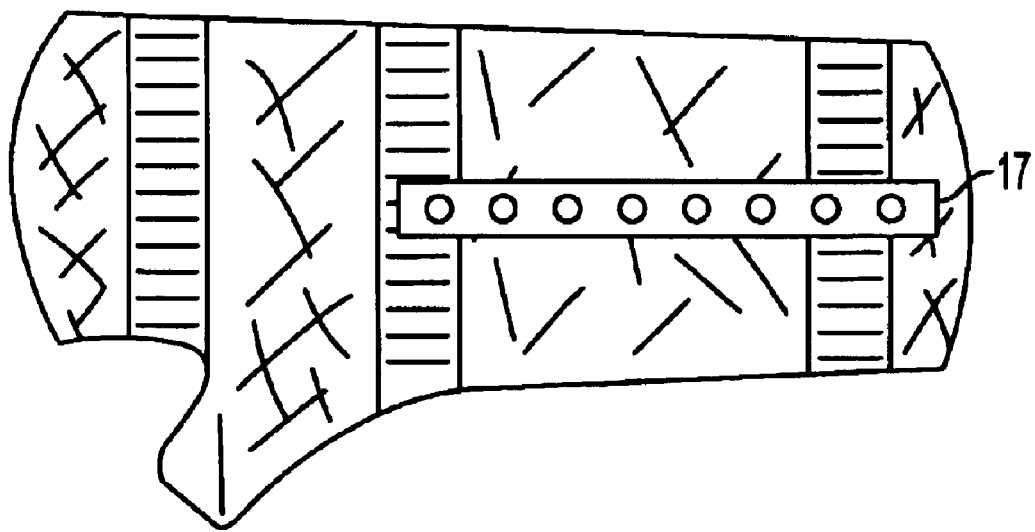
FIG. 4 is a bottom view of the second embodiment from FIG. 3, the illustrated embodiment having a longitudinally configured rigid mounting member mounted to the splint.

FIG. 4 is a bottom view of the embodiment from FIG. 3, the illustrated embodiment having the longitudinally attached rigid mounting member 17 mounted to the splint.

Figure 5:
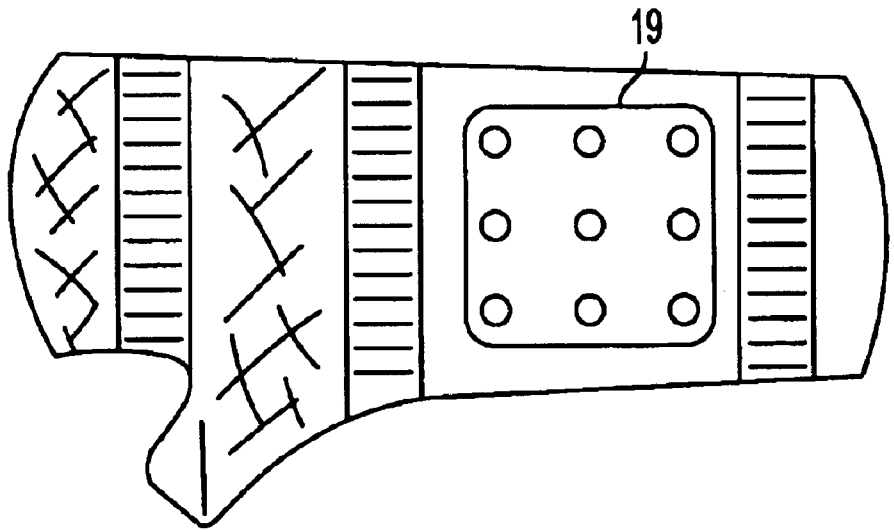
FIG. 5 is a bottom view of a third embodiment of a splint with a rigid mounting plate having a matrix of multiple mounting holes.

FIG. 5 is a bottom view of a third embodiment of a splint 5 with a mounting plate 19 having multiple sockets or threaded holes 15 arranged in a matrix. This embodiment provides the user with numerous choices, with respect to the attachment position of the gyroscope 3 (i.e., both transversely and longitudinally positioned).

Figure 6:
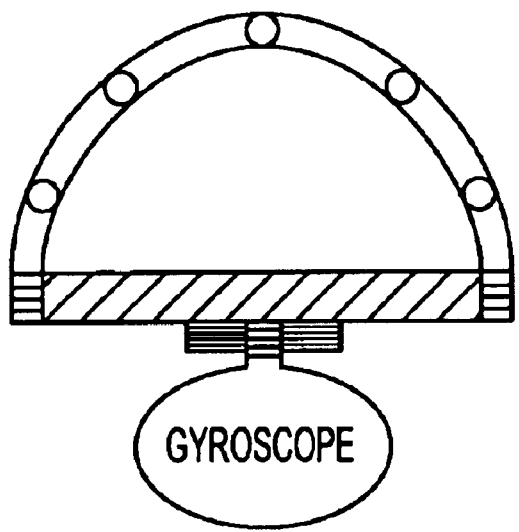
FIG. 6 shows a side cross-sectional view of the splint illustrated in FIGS. 1 through 5.

FIG. 6 shows a side cross-sectional view of the splint illustrated in FIGS. 1 through 5.

Figure 7:
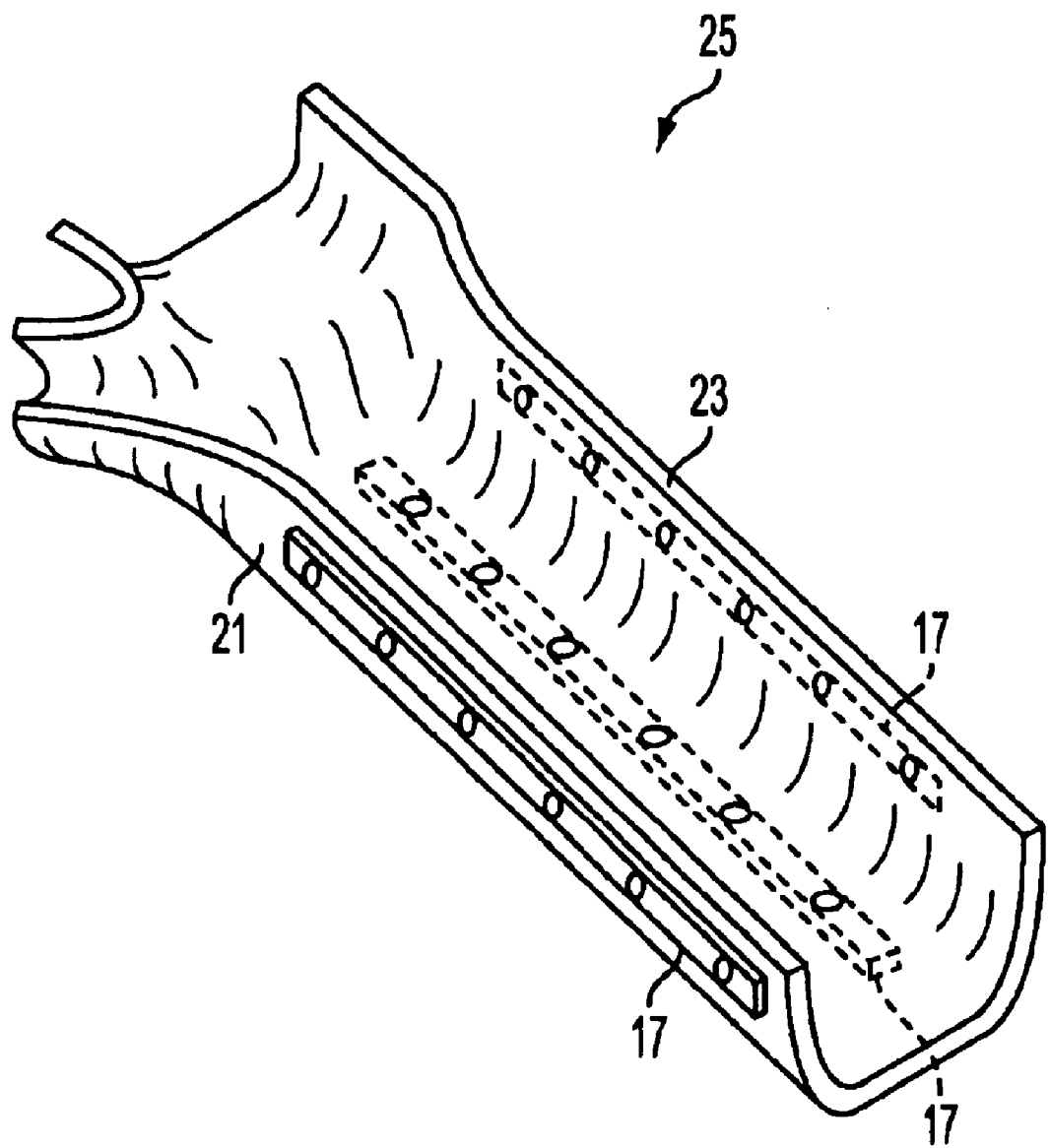
FIG. 7 illustrates an isometric perspective of a fourth embodiment of a splint having vertical sidewalls for receiving mounting bands.

FIG. 7 is a perspective of a fourth embodiment of the hand tremor stabilizer 1, which utilizes a splint 25 having vertical sidewalls 21, 23 for receiving longitudinally attached rigid mounting members 17. The vertical sidewalls 21, 23 in this embodiment provide the user with numerous gyroscope mounting positions that are useful for tuning (to be discussed later in specification) and for activities where clearance, with respect to the bottom side of the splint 25, is required. This embodiment may also utilize the transversely attached mounting members 13 or mounting plate 19 (not illustrated) as previously discussed in with respect to FIG. 1, FIG. 2, and FIG. 5.

Figure 8:
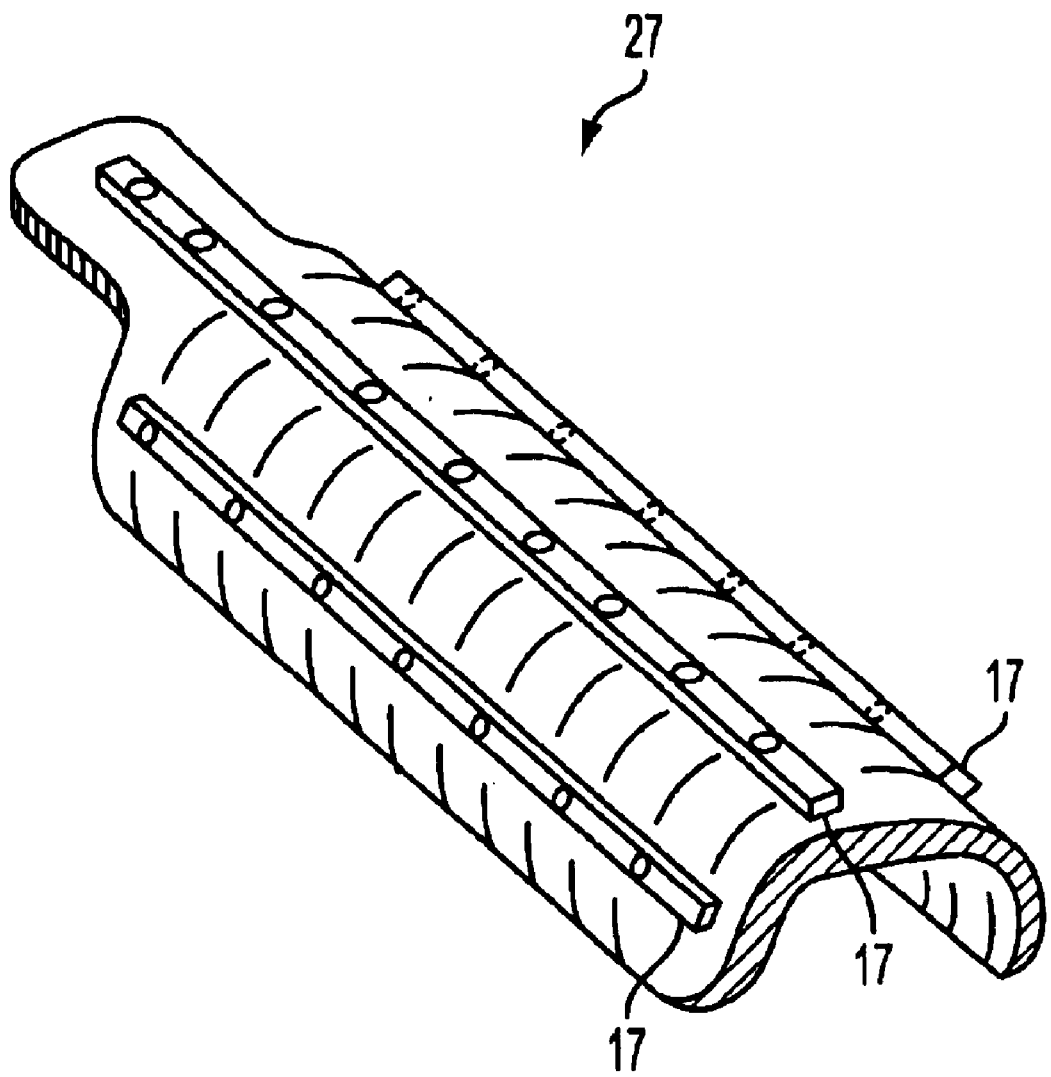
FIG. 8 illustrates an isometric perspective of a fifth embodiment of a splint configured to be attached to the top of the hand, wrist and arm areas, the splint having multiple rigid mounting member radially spaced on the upper surface of the splint.

FIG. 8 illustrates an isometric perspective of a fifth embodiment of a splint 27 configured to be attached to the top or "dorsal" portions of the hand, wrist and forearm region of the patient's body. This dorsal splint 27 is configured with multiple longitudinally attached rigid mounting members 17 which are radially spaced along the curvature or radius of the dorsal splint 27. This embodiment also provides the user with numerous gyroscope mounting positions that are useful for tuning (to be discussed later in specification) and for activities where clearance, with respect to the bottom side of the splint 27, is required.

Figure 9:
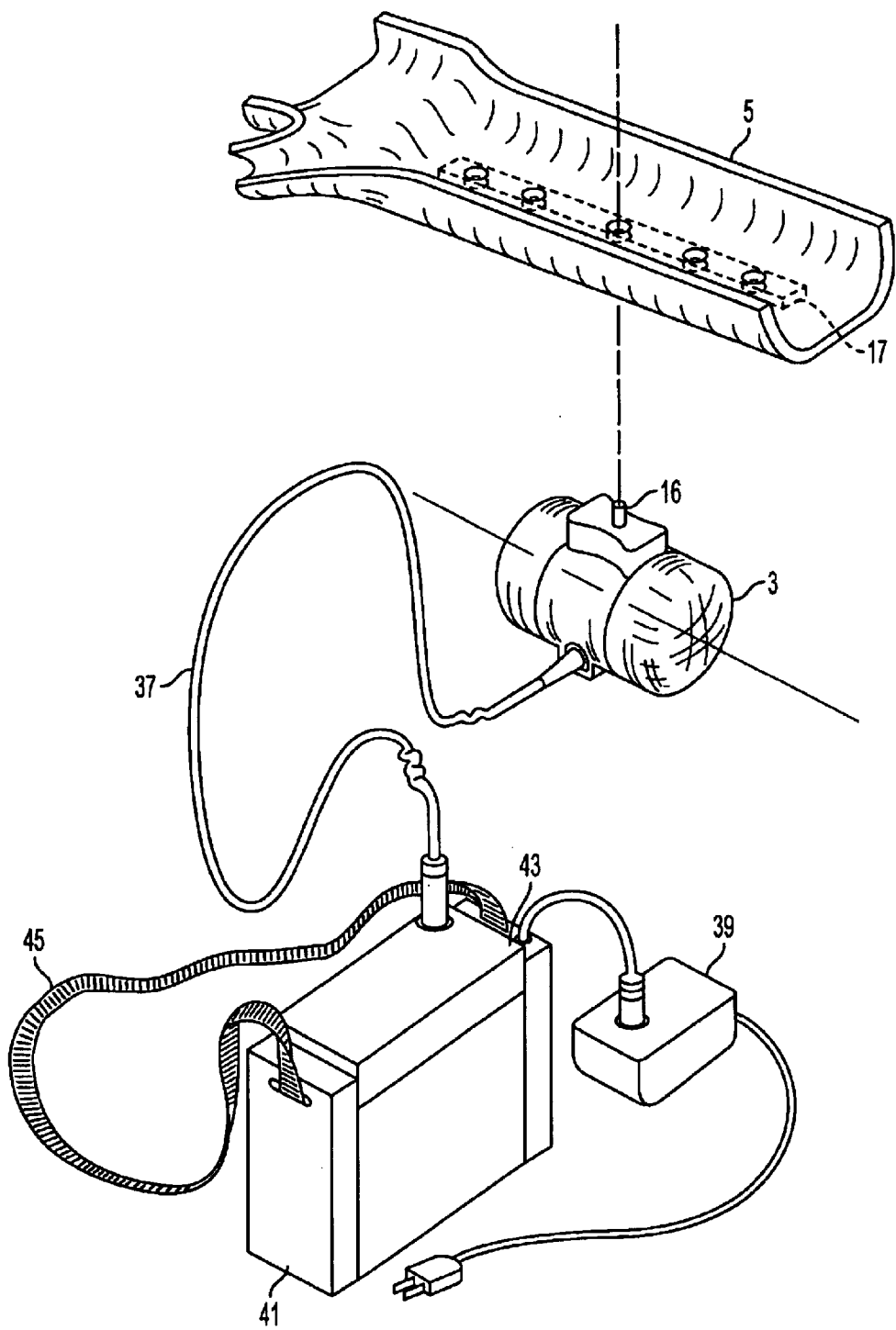
FIG. 9 illustrates an assembly having a gyroscope, battery powerpack, and charger accessories in accordance with the present invention.

FIG. 9 depicts an embodiment of hand tremor stabilizer 1 utilizing a gyroscope 3, such as a unit from the family of gyroscopes manufactured by Kenyon Laboratories LLC, 29 Plains Road, Essex, Connecticut 06426 (see http://www.ken-lab.com).

The gyroscope 3 is a small, battery-powered, pod-like case that screws into a receiving socket or threaded hole 15 (similar to that of a tripod socket) and of which is capable of stabilizing the patient's arm with only the splint 5 and gyroscope's 3 weight being supported by the user's arm. An advantage of utilizing the Kenyon gyroscope 3 as the stabilizing component of the present invention, is that it internally operates two gyroscopic flywheels (not illustrated) which are configured in parallel, yet in opposing axes to each other. When the flywheels are up to their normal operating speed, e.g., 22,000 rpm, the dual flywheel configuration resists both pitch and yaw when the gyroscope stabilizer 3 is configured "in line" with the longitudinal length of the user's arm length. Furthermore, the gyroscopes 3 all have springs within each unit that permit precession, as well as conduct electricity to the gyroscopic flywheels (not illustrated).

Any size gyroscope may be utilized as a stabilizer component of the present invention as long as the patient's arm can sustain the weight of the splint 5 and gyroscope 3. The heavier the gyroscope and/or increasing the rpms of the flywheel(s), the more countereffect the gyroscope will provide. The size of the gyroscope 3 should be selected depending on the degree of the patient's tremors, the type of activity the patient intends to accomplish, and the total amount of weight the patient may be required to support or is capable of supporting. For instance, if the patient's tremors are not substantial, it is more ideal to utilize the lightest and most compact sized gyroscope. If the patient's tremors are more violent, it is more appropriate to utilize a heavier gyroscope and/or one that has an increased rpm rate for its flywheel(s) 3, which is more resistant to stronger forces. Hereinbelow, an example of different gyroscopes 3 which may be utilized as the stabilizing component of the present invention, will be described.

A number of various sized gyroscopes 3 are available on the market. By way of example, Kenyon Labs provides a line of gyroscopes 3 which can be utilized with the present invention, including the "Explorer KS-2", "Universal KS-4", "Commander KS-6", and "Admiral KS-8", each of which are described herewith below.

The "Explorer KS-2" is the lightest and most compact gyroscope available from Kenyon Labs. This unit is ideal for patients that have weak tremors. It is capable of stabilizing an object weighing up to two pounds. The KS-2 has a 2.8" diameter, is 4.5" long, and weighs 1.5 lbs (24 oz.). It is powered by a KP-6 battery powerpack (also available from Kenyon Labs) which provides electricity at 115 volts, 400 Hz AC. The KS-2 requires 28 watts for starting and 20 watts for running after 12 minutes from start-up and can run on a fully charged KP-6 powerpack for 6 hours.

The "Universal KS-4" provides the lowest cost per device served. Ultra heavy metal gyro rims enable maximum stabilization in a minimum casing size. This unit would be ideal for stabilizing one's arm for an activity such as holding a camera to take pictures or shooting firearms. Hand held devices to four pounds can be stabilized by the KS4. It has a panning rate of 20 degrees per second. This unit has a 2.8" diameter and is 4.5" long. The KS-4 weighs 2.13 lbs (34 oz.) and is powered by a KP-4 battery powerpack which is also available from Kenyon Labs. The KP-4 provides electricity at 115 volts and 400 Hz AC. The KS-4 requires 14 watts for starting, 8 watts for running after 10 minutes from start-up, and can run on a fully charged KP-4 power pack for 5 hours.

The "Commander KS-6" is a more robust gyroscope 3 which would be proper to use when the patient's tremors are more violent and frequent and where the patient's arms require significant stabilization. The KS-6 provides almost twice the stabilization of the KS-4. It has a panning rate of 20 degrees per second. However, the tradeoff is that the unit's size and weight tends to be more burdensome. This unit is powerful enough to dampen active shaking and tremors, without, the loss of the freedom of motion for the hand, wrist and arm and the object the user may be holding. The KS-6 unit adds stabilization as high as 6 lbs. It has a 3.4" diameter, is 5.8" long and weighs 3.25 lbs. (52 oz.). The KS-6 is powered by a KP-6 power pack which is also manufactured by Kenyon Labs. The KP-6 battery powerpack provides electricity at 115 volts and 400 Hz AC. The KS-6 requires 28 watts when starting, runs on 20 watts after 10 minutes, and can run for 2.5 hours on a fully charged KP-6 powerpack.

The "Admiral KS-8" is the heaviest and most powerful gyroscope manufactured by Kenyon Labs. This unit can be utilized in scenarios where the patient has the most violent and severe tremors, but yet still has the arm strength to be able to support the heavier weight of the KS-8, which is 5.13 lbs (82 oz.). This unit is capable of stabilizing handheld equipment weighing up to 8 to 12 pounds. The KS-8 has a panning rate of 30 degrees per second. Through the use of heavy metal tungsten flywheels, the effect of two KS-6 units can be achieved in a standard KS-6 housing, with no increase in running power required. The KP-6 battery powerpack provides electricity at 115 volts and 400 Hz AC. The KS-8 requires 28 watts when starting, runs on 20 watts after 12 minutes, and can run for 2.5 hours on a fully charged KP-6 powerpack.

It is noted that, while for convenience of explanation and illustration, the instant invention discusses, by way of example, the gyroscopes manufactured by Kenyon Labs, this disclosure is not intended as limiting, and it is understood that other gyroscopes produced by other manufacturers, including one, two, and three flywheel gyroscopes, are likewise within the purview of the instant invention and can be utilized in combination with the features of the instant invention.

Now referring back to FIG. 9, it can be seen that the gyroscope stabilizer 3 can be powered to be run off of a portable battery power pack 41 (e.g., 12 volt powerpack, manufactured by Kenyon Labs), which may even have a shoulder strap 45 for ease of portability. Thus, with the gyroscope 3 attached to the splint 5 and the battery powerpack 41 attached to one's shoulder (or in a carpenter's belt or any other holding device), the patient has complete freedom to move about. Some gyroscope stabilizers 3 may also utilize AC electricity (e.g., 400 Hz). In this event, a small inverter 43 is on top of the battery 41 to access its DC power. The portable battery powerpack 41 may be charged with a battery charger 39, which may be an overnight charger. Moreover, one can bypass the battery powerpack 41 by using external 12 volt power, such as may be provided in a plane, train, car, or boat.

The gyroscope 3 may take a short period of time to achieve full operating rpm, e.g., 5 to 7 minutes. Therefore, the gyroscope 3 may be attached to the splint 5 before running up, and left undisturbed until it has reached it's maximum running speed. This can be noted by the sound of the flywheels as they run up. The gyroscope 3 will increase in pitch as it gains speed, and one can even hear when the unit changes from its starting winding on the motor to its running winding, which draws less power. Then the splint 5 with the attached and fully running gyroscope 3 may be carefully attached the user's arm, by the user or perhaps with assistance by another person.

Generally gyroscopes 3 have no brakes within them, so after a unit is no longer receiving power, it will stabilize while it freewheels down to a stop. In this regard, the stop time is dependent upon the size and speed of the gyroscope flywheels, e.g., it may take up to an hour for larger gyroscopes to stop spinning, and progressively less time to free wheel down.

Figure 10:
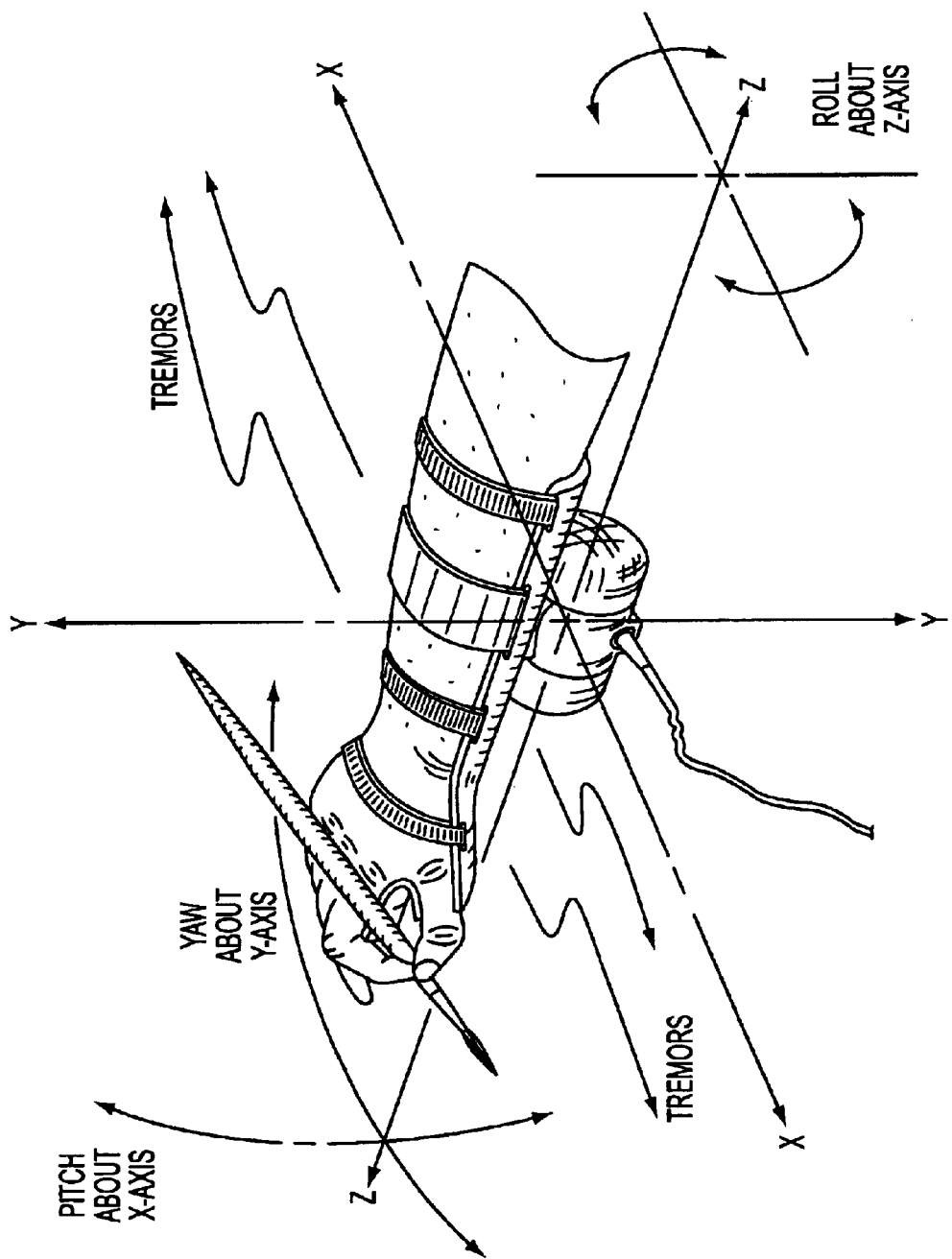
FIG. 10 illustrates how the gyroscope countereffects tremors with respect to yaw and pitch when configured parallel to the longitudinal axis of the splint (i.e. "in-line")

FIG. 10 illustrates an embodiment of the present invention in which the gyroscope 3 is attached to the splint 5 from underneath ("volar perspective") in a parallel configuration with respect to the longitudinal length of the user's arm (as referred to as an "in-line" configuration). As discussed previously, if the gyroscope 3 is mounted in this manner, it will resist forces with respect to pitch and yaw. In terms of axes, the gyroscope 3 will resist movement about the x and y axes. Therefore, it can be seen that if a patient suffers from tremors which are substantially isolated about the y-axis, the aforementioned embodiment will effectively stabilize the patient's arm such that the patient will be able to prevent any unwanted yaw in his/her hand, wrist, and arm area. In a similar manner, it can also be seen that if a patient suffers from tremors which are substantially isolated about the x-axis, the aforementioned embodiment will effectively stabilize the patient's arm such that the patient will be able to prevent any unwanted pitch. Ideally, the embodiment of FIG. 10 can be utilized when the patient's tremors are both substantially isolated to the x and y axes. However, there will be no stabilization with respect to roll about the z-axis.

Should one need to also resist roll or movement about the z axis, the addition of a second gyroscope 3 perpendicular to the first, either in a "T or vertical" configuration with respect to the first is needed. Such embodiments will be described in further detail later on in the specification (See FIG. 12(c), FIG. 13(c), FIG. 14(c)).

Figure 11:
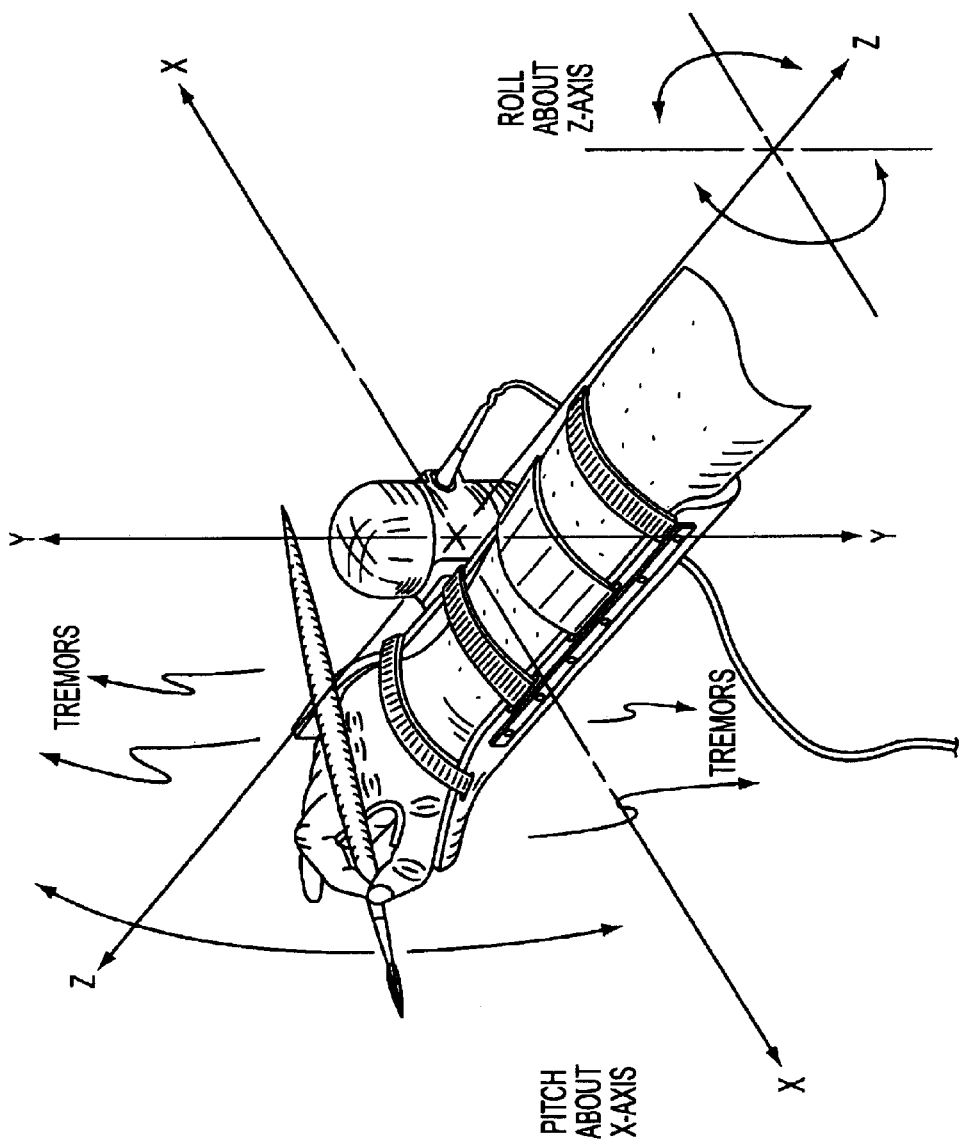
FIG. 11 illustrates how the gyroscope countereffects tremors with respect to pitch and roll when configured perpendicular to the longitudinal axis of the splint (i.e. "vertical configuration"

FIG. 11 illustrates another embodiment of the present invention. In this embodiment, the gyroscope 3 is attached in a vertical configuration with respect the user's arm when the user's arm is held outward in a horizontal manner. If the gyroscope 3 is mounted in this manner, it will resist forces with respect to roll and pitch. Thus, in terms of axes, the gyroscope 3 will resist movement about the x and z axes.

Therefore, it can be seen that if a patient suffers from tremors which are substantially isolated about the x-axis, the embodiment of FIG. 11 will effectively stabilize the patient's arm such that the patient will be able to prevent any unwanted roll. In a similar manner, it can also be seen that if a patient suffers from tremors which substantially are isolated about the z-axis, the aforementioned embodiment will effectively stabilize the patient's arm such that the patient will be able to prevent any unwanted pitch. Ideally, the aforementioned embodiment can be utilized when the patient's tremors are both substantially isolated to the x and z axes. However, there will be no stabilization with respect to yaw about the y-axis.

Another feature of the present invention with regard to adjustability and tuning and adjustability is the capability to either intentionally balance the center of gravity of the hand tremor stabilizer 1, or to intentionally offset the placement of the gyroscope 3 on the splint 5 so that the hand tremor stabilizer 1 is purposely out of balance. As a result, a pulling or tipping force may be induced.

Referring back to FIG. 10, it can be seen that the gyroscope 3 is mounted such that the hand tremor stabilizer 1 is in a balanced configuration. With such a configuration, there is no pulling force induced about the z-axis or along the xz-plane, or about a combination of both. Hence, this configuration, as already discussed above, is ideally suited for countereffecting tremors about the x-axis (pitch) and y-axis (yaw). However, even though the embodiment illustrated in FIG. 10 is balanced, it should be remembered that the weight of the gyroscope 3, will always result in a downward pulling force due to gravity. Hence, when selecting the size of the gyroscope 3 to be utilized, the user will have to take into consideration the trade-offs between the weight of the gyroscope 3 utilized and the stabilization force that is require to stabilize the user's tremors.

In the same regard, by referring back to FIG. 11, it can be seen that the gyroscope 3 is mounted such that the hand tremor stabilizer 1 is in a non-balanced configuration. Thus, this configuration, not only will inhibit unwanted tremor movement with respect to roll and pitch, but it is also tuned such that there will be a tipping or pulling force induced about the z-axis (roll) or along the xz-plane, or about a combination of both. As it can be seen then, the present invention has numerous permutations and combinations in which it may be adjusted and tuned to countereffect a patients tremors.

Hence, not only is the manner in which the gyroscope 3 oriented with respect to the splint 5 (i.e flywheel spin direction) useful for countereffecting predictable tremors, but also the placement of the gyroscope 3 with respect to weighting and center of gravity is useful in countereffecting predictable tremors. As a general rule, the more balanced the hand tremor stabilizer 1 is with respect to center of gravity, the easier it will be for the user to point, move, or guide the hand tremor stabilizer 1 in a motion of which the user intends. For instance, if the patient requires a steady hand for painting, a balanced setup may be the best approach. However, if the patient has tremors in which his/her arm is constantly being trajected in a certain undesirable motion, then the hand tremor stabilizer 1 can be tuned, or setup off balanced such that the hand tremor stabilizer 1 will pull or "pan" towards a specific direction. The overall effect and end result is an adjustable and tunable hand tremor stabilizer that can be setup specifically such that it countereffects each patient's unique needs.

FIGS. 12(a)–(c) through 15(a)–(c) are provided to illustrate just a few of the numerous permutations and combinations in which the hand tremor stabilizer 1 may be adjusted and tuned to countereffect a patient's tremors. The resulting countereffects of each embodiment, as a result of its "tuned setup" will be described herein below. For illustrative purposes only, each embodiment will be described assuming that the tunable hand tremor stabilizer 1 is on the patient's right hand/wrist/arm. Needless to say, the present invention is designed to be worn on either the left arm or right arm, although a right handed splint 5 has been illustrated.

Figure 12A:
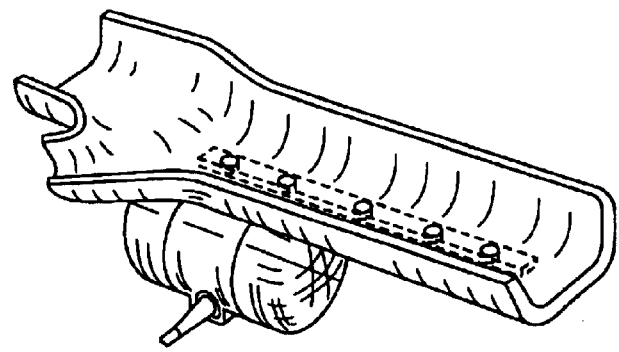
FIGS. 12(a)–(c) provide various mounting configurations for the gyroscope, and in particular, illustrates several embodiments having the gyroscope mounted parallel to the longitudinal axis of the splint (i.e., "inline configuration")
Figure 12B:
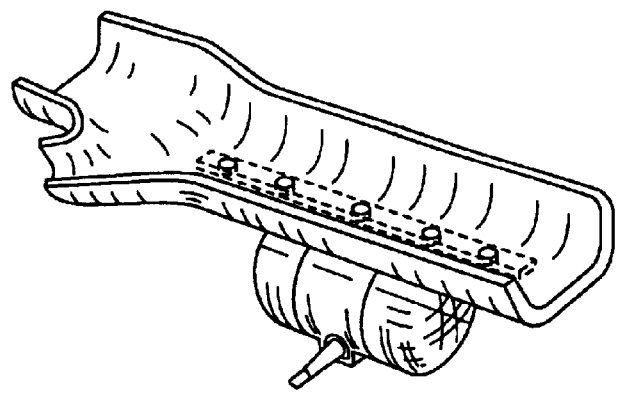
Figure 12C:
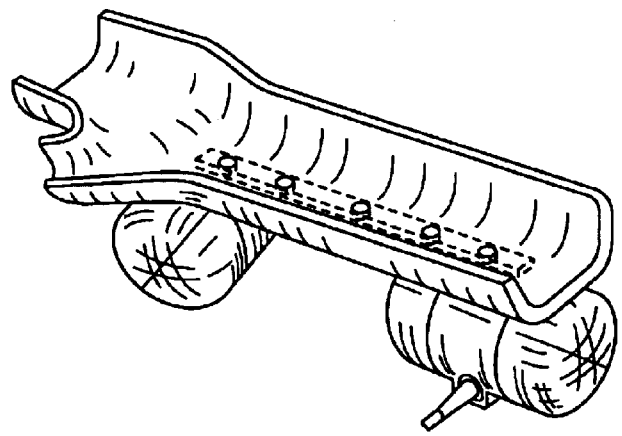

FIGS. 12(a)–(c) illustrates the hand tremor stabilizer 1 which utilizes a splint 5 having a longitudinally attached rigid mounting member 17 and one or two gyroscopes 3. In this "in-line" configuration, it can initially be observed that the adjustability of the center of gravity is limited along the longitudinally attached rigid mounting member 17. Note, if one desired to be able to adjust the balance and center of gravity in the transverse direction, and still maintain a mounting position from underneath the splint, than the splint 5 depicted in FIG. 2 or FIG. 5, both of which have transversely spaced receiving sockets or threaded holes 15 could be utilized instead (not illustrated).

With respect to both FIG. 12(a) and FIG. 12(b), the tuning and balancing characteristics herein are described below. In FIG. 12(a), since the gyroscope 3 is mounted forward towards the wrist, the user will experience a reduced countereffect to pitch about the x-axis because the center of gravity is essentially under the user's wrist. As a result the hand tremor stabilizer 1 will be more inclined to dip downwards about the x-axis since the weight of the gyroscope 3 is positioned towards the distal end of the hand tremor stabilizer 1. This can be compared to a "balanced" configuration illustrated in FIG. 12(b) which is essentially the same embodiment depicted in FIG. 10. However, it should be kept in mind that both configurations will still countereffect pitch about the x-axis and yaw about the y-axis.

FIG. 12(c) utilizes two gyroscopes 3. The end result of such a configuration is a balanced effect that does not induce any pull to the left or right along the x-axis or roll about the z-axis. The stabilization effect, nevertheless, is stabilization with respect to yaw, pitch, and roll. Hence, a three dimensional countereffect results. Furthermore, since the most forwardly mounted gyroscope 3 is transversely oriented (otherwise referred to as a "T-configuration"), a double countereffect with respect to yaw results. However, the tradeoff with respect to the two gyroscope configuration is obviously a weight disadvantage. Such a weight disadvantage may be mitigated through the use of smaller gyroscopes 3 which weigh less.

Figure 13A:
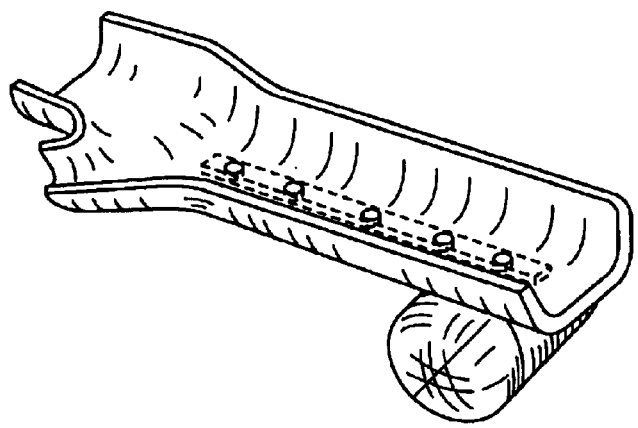
FIGS. 13(a)–(c) provides various mounting configurations for the gyroscope, and in particular, illustrates several embodiments of the gyroscope mounted transversely to the longitudinal axis of the splint (i.e, T-configuration")
Figure 13B:
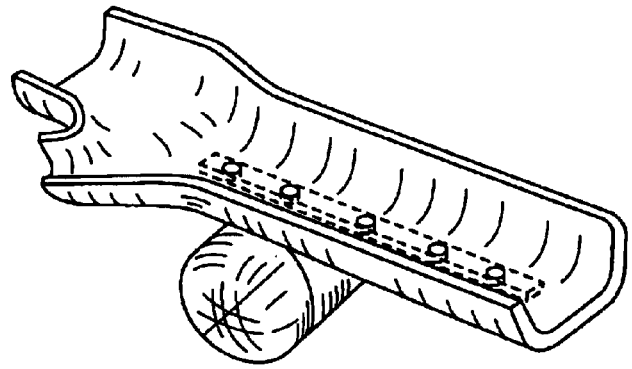
Figure 13C:
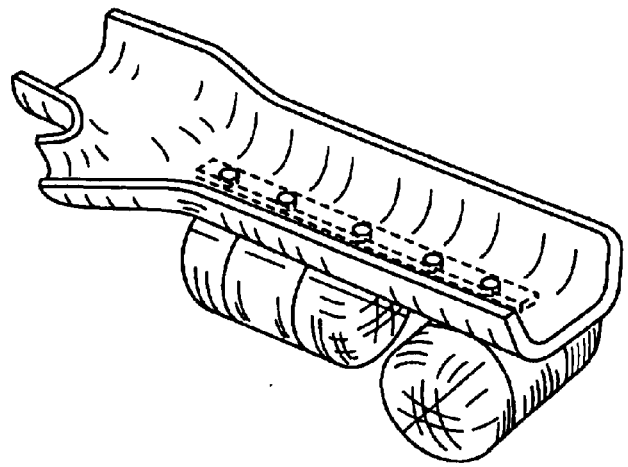

FIGS. 13(a)–(c) further disclose embodiments which utilized the "T-configuration" described above. By the utilizing the T-configuration, unwanted tremors with respect to roll and yaw may be countereffected. FIG. 13(a) discloses an out of balanced embodiment. Since the gyroscope 3 is positioned closer to the patient's elbow, it can be expected that the stabilization countereffect induced for the gyroscope 3 will be focused towards the elbow and there will be less countereffect near the user's hand.

With respect to FIG. 13(b), it is apparent that the hand tremor stabilizer 1 is much more balanced than the embodiment shown in FIG. 13(a). FIG. 13(c) will yield a similar effect to the embodiment depicted in FIG. 12(c), which is stabilization for unwanted tremor motion in all three dimensions, yaw, pitch, and roll. However, since the most forward gyroscope 3 (i.e. towards the user's wrist) is actually closer to the user's elbow in this embodiment as compared to FIG. 12(c), it can be expected that the combination of the weight of the two gyroscopes 3 with the center of gravity being more towards the user's elbow, will yield a downward pulling force towards the elbow of the user. As a result, the embodiment depicted in FIG. 13(c) will not countereffect pitch as effectively as the embodiment in FIG. 12(c). This result may be a desired tuning characteristic if a patient has unwanted tremors which are focused more towards the patient's elbow. Or perhaps, the configuration depicted in FIG. 13(a) would be suited for a patient who requires his/her hand to be propped up higher than his/her elbow. Nevertheless, the weight of two gyroscopes 33 is a tradeoff the patient must consider.

Figure 14A:
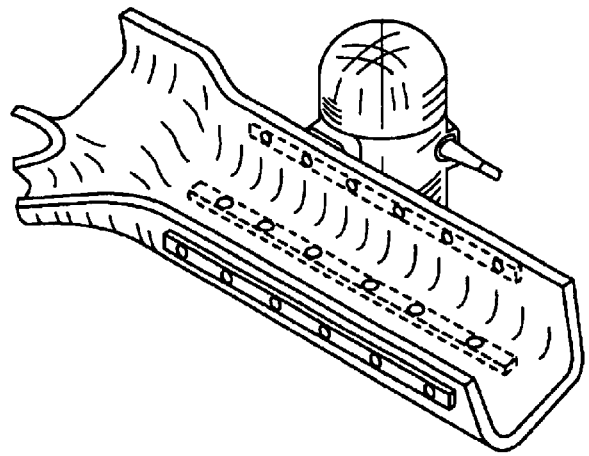
FIGS. 14(a)–(c) provides various mounting configurations for the gyroscope, and in particular, illustrates several embodiments of the having the gyroscope mounted to vertical sidewalls of a splint.
Figure 14B:
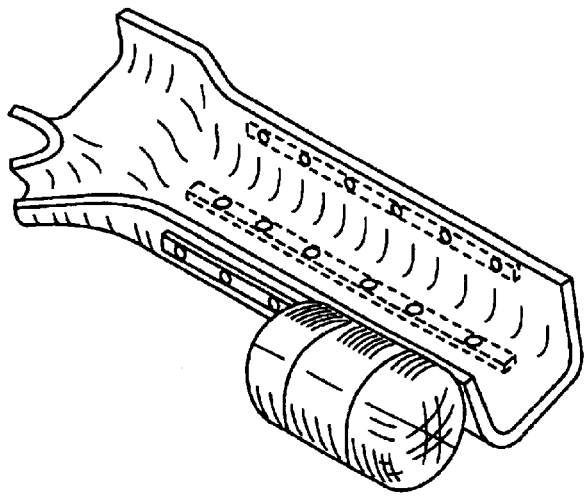
Figure 14C:
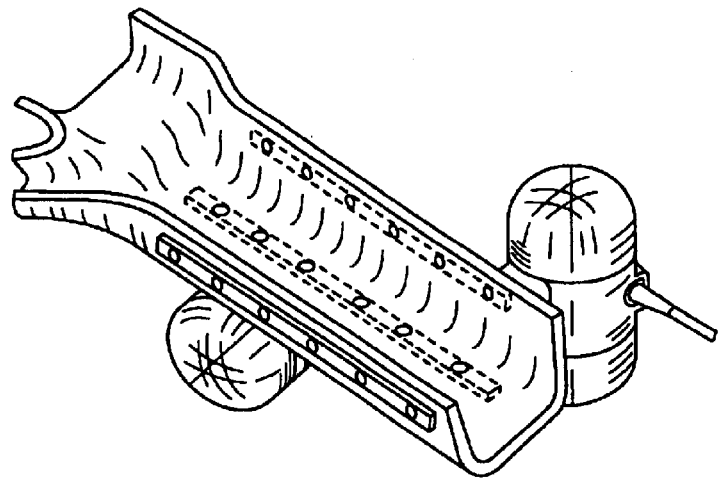

FIGS. 14(a)–(c) illustrate embodiments which utilize the splint 25 which has vertical sidewalls 21, 23. FIG. 14(a) depicts an embodiment which utilizes a vertically oriented gyroscope 3 mounted on the right vertical sidewall 23, which is essentially the same embodiment described in FIG. 11. As described previously, with this embodiment, not only will the gyroscope 3 resist roll and pitch, but also there will be a tendency for the hand tremor stabilizer to pull downward to the right. This results in a mitigation of the countereffect to roll, in particular, about the z-axis. Or to put it another way, the offset will induce more roll about the z-axis in a clockwise direction and decrease the countereffect to roll in the counterclockwise direction about the z-axis. Thus, this embodiment would be useful in stabilizing a patient's hand which not only shakes about the z-axis, and of which also the patient's hand moves up and down about the x-axis, but it also will effectively counteract the patient's unwanted tremors which tend to twist the user's hand/wrist/arm upwards and to the left of towards his/her body.

FIG. 14(b) is in the "in-line" configuration which dictates that the hand tremor stabilizer 1 will resist unwanted tremor movement with respect to pitch and yaw. Since the gyroscope 3 is mounted on the left vertical sidewall 21 of splint 25, there will be an unbalanced center of gravity. Such a configuration will result in the inducement of a roll about the z-axis in a counter clockwise direction. In FIG. 14(c), a two gyroscope configuration is utilized. The overall countereffect is resistance to roll, yaw, and pitch. If this configuration was perfectly balanced, it would result in a double roll countereffect. However, since one of the gyroscopes 3 is mounted on the right vertical sidewall 23, the double roll countereffect is somewhat modified. In particular, there will be more countereffect to roll about the z-axis in a clockwise direction, than the counterclockwise position. Nevertheless, countereffect to roll will be present about the z-axis in both direction since the aforementioned embodiment utilizes two gyroscopes 3.

Figure 15A:
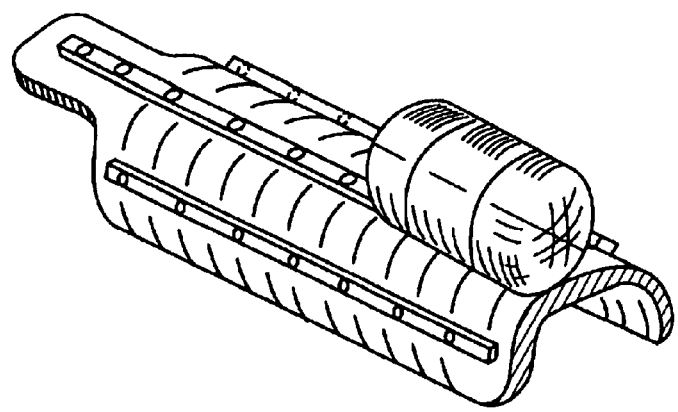
FIGS. 15(a)–(c) provides various mounting configurations for the gyroscope, and in particular, illustrates several embodiments of the gyroscope mounted to a splint configured to be attached to the top of the hand, wrist and arm areas.
Figure 15B:
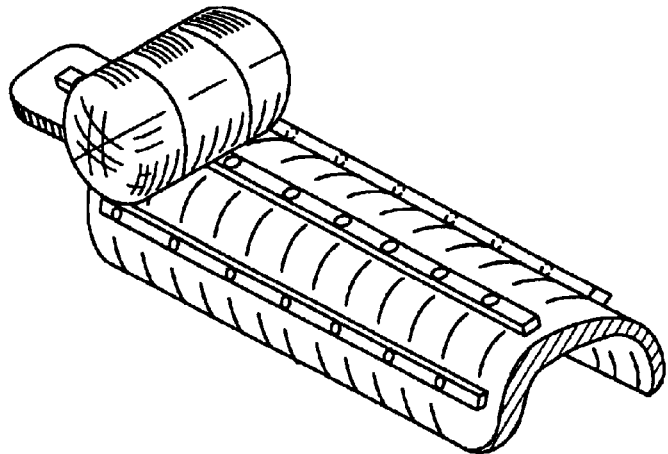
Figure 15C:
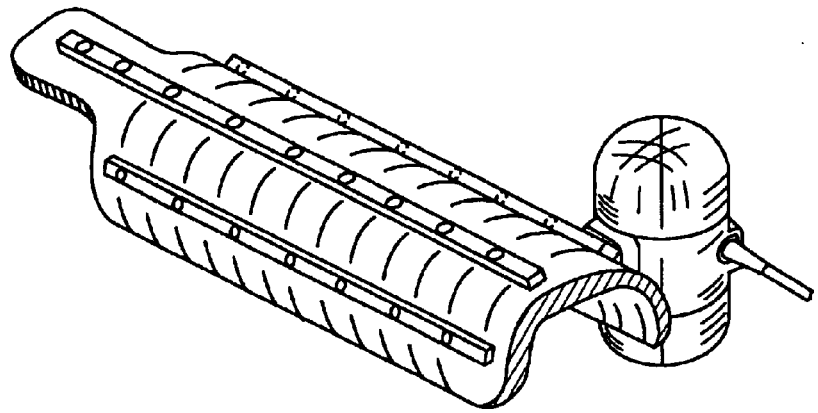

FIGS. 15(a)–15(c) discloses several embodiments which utilize the dorsal mounted splint 27 in combination with the gyroscopes 3. For instance, in FIG. 15(a), the gyroscope 3 is mounted on the longitudinally attached rigid mounting member 17 which is centered on the top of the splint 27. Since the gyroscope 3 is configured "in-line", the gyroscope 3 will countereffect undesired tremors with respect to yaw and pitch. Furthermore, since the gyroscope 3 is positioned closer to the elbow, it can be expected that the countereffect of the gyroscope 3 will be more focused towards the elbow and will have less effect on stabilizing the hand.

FIG. 15(b) discloses another embodiment which incorporates the "T-configuration", i.e, the gyroscope 3 is transversely mounted on the longitudinally attached rigid mounting member 17 which is centered on the top of the splint 27. In this circumstance, the patient can expect to have unwanted tremors stabilized with respect to roll and yaw. Furthermore, since the gyroscope 3 is mounted closer to the hand, the user can expect to have more overall stabilization effect focused near the patient's hand and wrist.

FIG. 15(c) discloses an embodiment which utilizes an offset and unbalanced setup. Since the gyroscope 3 is in the vertical configuration, it can be expected that the hand tremor stabilizer 1 will resist roll and pitch. However, due to the offset and unbalanced positioning of the gyroscope 3, it can be expected that there will be some pull downward to right. This configuration would be useful if the patient's tremors requires his/hers hand to be propped up and flared outward away from the body.

Figure 16A:
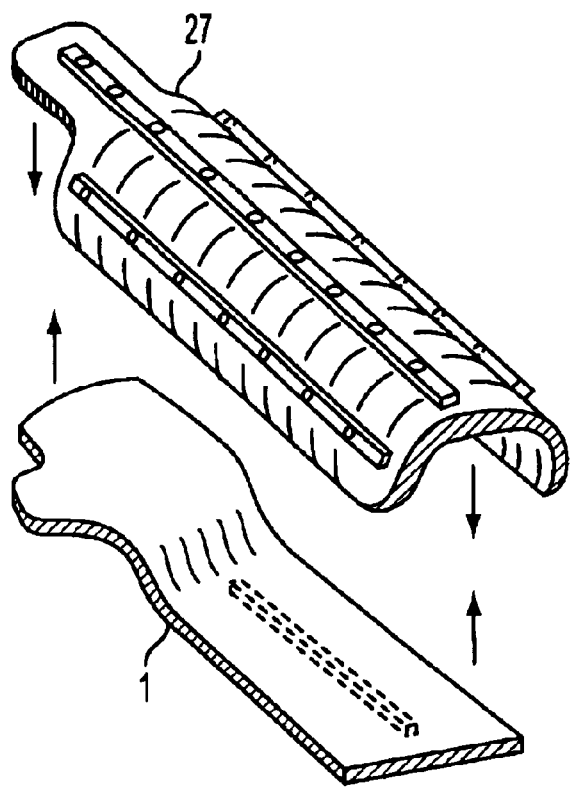
FIGS. 16(a)–(b) provide a sixth embodiment which allows multiple gyroscopes to be mounted from the volar and dorsal perspective of the hand, wrist, and arm.
Figure 16B:
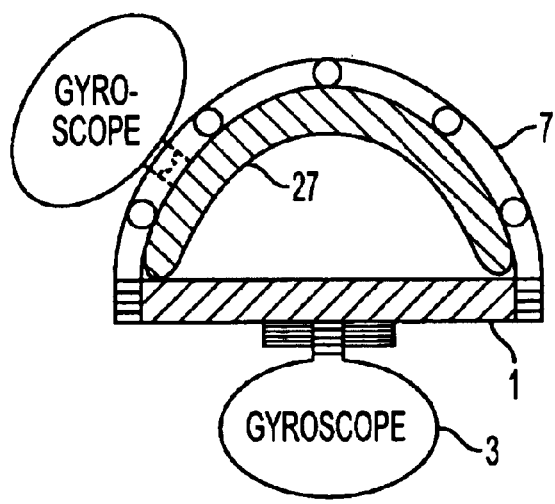

FIGS. 16(a)–(b) provides a sixth embodiment which allows multiple gyroscopes 3 to be mounted from the both volar and dorsal perspective of the hand, wrist, and arm. This embodiment utilizes a clamshell configuration in which the volar mounted splint 5 (illustrated in FIGS. 1–5) acts as a base and the dorsal mounted splint 27 acts the top of the clamshell. This embodiment allows the patient to place a gyroscope 3 simultaneously on underneath and above his/her arm as shown in FIG. 16(b). The splints 5 and 27 are clamped together utilizing the same fastening hardware that is utilized individually for either splint 5 or splint 27. In particular, primary mounting band 7 and VELCRO secondary mounting strips 9 are provided for securing splint 5 and 27 together with to the patient's hand, wrist, and forearm sandwiched in between. Splints 5 and 27 may also be attached to the patient using other known techniques, such as elastic bands, adjustable belts, straps or any other splint fastening methods known in the art.

Figure 17:
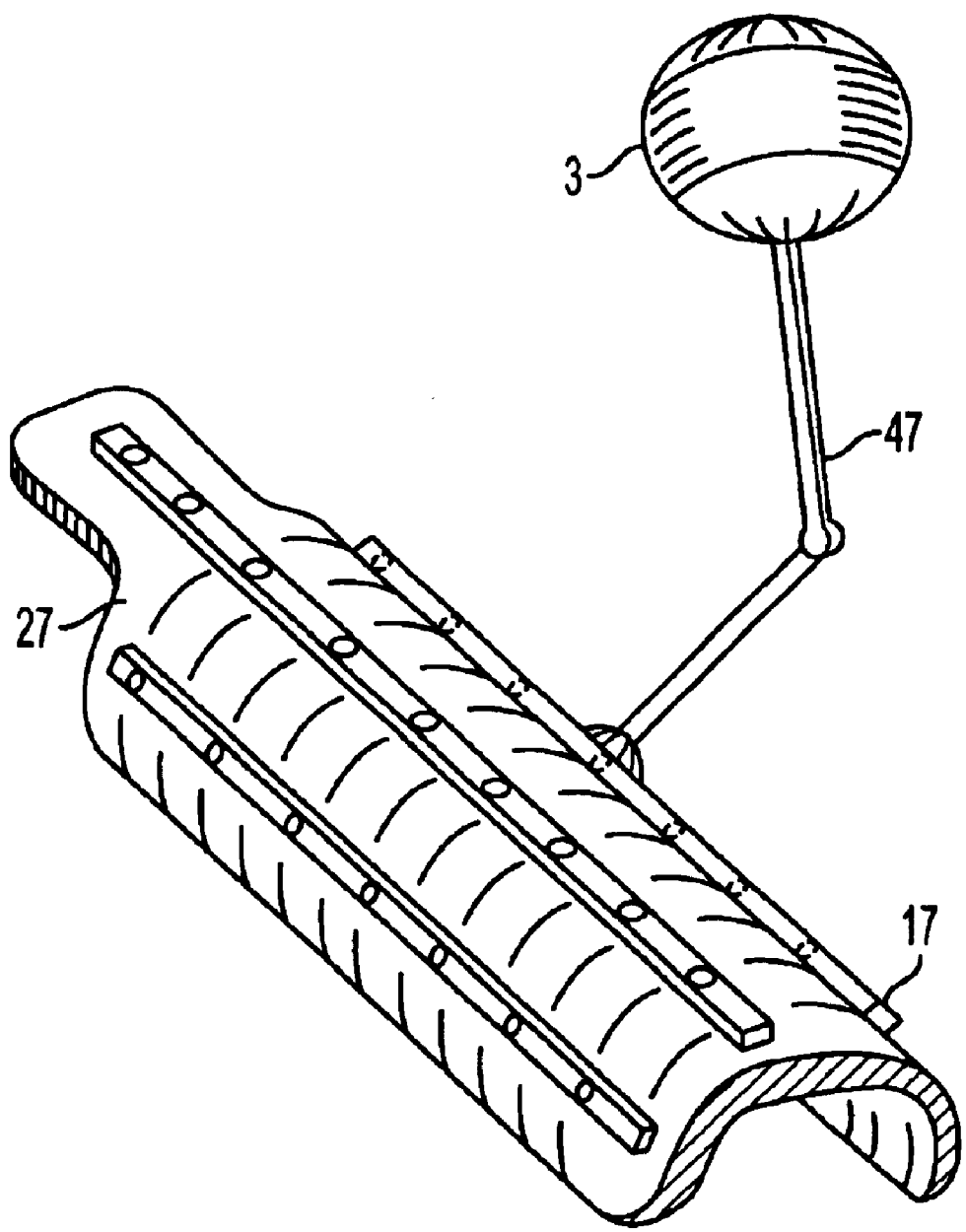
FIG. 17 depicts a seventh embodiment which utilizes an articulated member to attach the gyroscope.

FIG. 17 depicts a seventh embodiment which utilizes an articulated member to attach the gyroscope 3. An articulated member 47 may be used to position the gyroscope 3 in any position that the articulated member permits. The articulated member 47 may have several degrees of freedom, including but not limited to swivels, hinges, telescoping members, etc., all of which are well known in the art. As a result, the aforementioned embodiment greatly enhances the patient's ability to tune his/her adjustable and tunable hand tremor stabilizer 1 according to the patient's tremors and planned activity.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF PARTS AND REFERENCE NUMBERS

1. Adjustable and tunable hand tremor stabilizer
3. Self-contained gyroscope
5. Splint
7. Primary mounting band
9. Secondary mounting band 11. Gyroscope mounting fitting
13. Transversely attached rigid mounting member
15. Receiving socket or threaded hole
16. Threaded male fastener
17. Longitudinally attached rigid mounting member
19. Rigid mounting plate with multiple sockets or threaded holes
21. Left vertical sidewall
23. Right vertical sidewall
25. Splint with vertical sidewalls
27. Dorsal mounted splint
28. Wrist portion
35. Stabilizer axis
37. Power cord
39. Battery charger
41. Battery powerpack
43. Inverter
45. Shoulder strap
47. Articulated member

What is claimed:

1. A tunable and adjustable device for stabilizing tremors, the device comprising:
    a rigid splint for receiving a patient's hand, wrist and forearm; and
    at least one gyroscope removably and rigidly attachable to said splint and positionable for countereffecting the tremors.

2. The device according to claim 1, further comprising at least one mounting band for securing said splint to the patient's hand, wrist, and forearm.

3. The device according to claim 1, further comprising at least one rigid mounting member attached to said splint, said at least one mounting member having at least one of receiving sockets or threaded holes for receiving a gyroscope mounting fitting.

4. The device according to claim 3, said at least one mounting member attached to one of a bottom, top, and side of said splint.

5. The device according to claim 3, said at least one mounting member attached to said splint in a transverse orientation with respect to a longitudinal length of said splint.

6. The device according to claim 5, said at least one mounting member comprising a plurality of mounting members attached to said splint in a transverse orientation with respect to the longitudinal length of said splint.

7. The device according to claim 3, said at least one mounting member being attached in a longitudinal orientation with respect to a longitudinal length of said splint.

8. The device according to claim 7, said at least one mounting member comprising a plurality of said mounting members attached to said splint in a longitudinal orientation with respect to the longitudinal length of said splint.

9. The device according to claim 1, further comprising a rigid plate attached to said splint, said rigid plate having a plurality of receiving sockets or threaded holes for receiving a gyroscope mounting fitting, said receiving sockets or threaded holes being positioned in a matrix to provide multiple mounting positions in both a transverse and longitudinal orientation with respect to a longitudinal length of said splint.

10. The device according to claim 1, said splint having vertical sidewalls and at least one rigid mounting member attached to at least one sidewall, said mounting member having at least one receiving socket or threaded hole for receiving a gyroscope mounting fitting.

11. The device according to claim 1, said splint being structured to be attached to a dorsal portion of the patient's hand, wrist and forearm.

12. The device according to claim 11, further comprising a plurality of mounting members attached to said splint in a longitudinal orientation with respect to the longitudinal length of said splint, said mounting members each having a plurality of receiving sockets or threaded holes for receiving a gyroscope mounting fitting.

13. The device according to claim 1, further comprising a power supply for providing power to said at least one gyroscope.

14. The device according to claim 13, said power supply comprising a battery powerpack connected to said gyroscope by a power cord.

15. The device according to claim 1, wherein said at least one gyroscope resists motion in at least one of one, two, and three directional planes.

16. The device according to claim 1, wherein said at least one gyroscope resists motion in at least one of about an x-axis, y-axis, and z-axis.

17. The device according to claim 1, said at least one gyroscope having at least one of one, two, and three flywheels for countereffecting tremors.

18. The device according to claim 1, said splint comprising a pair of splints configured in a clamshell orientation.

19. The device according to claim 3, further comprising an articulated member connecting said at least one gyroscope to said at least one rigid mounting member.

20. The device according to claim 19, said articulated member capable of being adjusted and positioned by at least one of swiveling, telescoping, and rotating about a hinge, before the position of said articulated member is rigidly secured such that said at least one gyroscope is rigidly supported to said splint.

21. The device according to claim 1, said at least one gyroscope having at least one flywheel with an adjustable spin rate.

22. A method for tuning and adjusting a device for stabilizing tremors, the device comprising a rigid splint for receiving a patient's hand, wrist and arm and at least one gyroscope removably and rigidly attached to said splint for countereffecting the tremors, the method comprising:
    attaching the splint to the patient's hand, wrist, and arm that he/she intends to use for at least one activity; and
    attaching and positioning the at least one gyroscope to the splint in at least one location which countereffects the patient's tremors.

23. The method according to claim 22, wherein the attaching and positioning is based upon input from dynamic characteristics of the patient's tremors and the at least one activity the patient intends to perform with his/her hand, wrist, and arm which is subject to tremors.

24. The method according to claim 22, further comprising operating the at least one gyroscope to countereffect the patient's tremors while the patient performs the at least one activity with his/her hand, wrist, and arm which is subject to tremors.

25. The method according claim 22, wherein the attaching and positioning comprises mounting the at least one gyroscope to the splint so that the splint and at least one gyroscope are balanced as an entire unit.

26. The method according to claim 22, wherein the attaching and positioning comprises mounting the at least one gyroscope to the splint in an out of balance position to induce at least one of a pulling, tipping, and rolling force in a desired direction.

27. The method according to claim 22, wherein the attaching and positioning comprises orienting the at least one gyroscope such that tremors that at least one of pitch about an x-axis, yaw about a y-axis, and roll about a z-axis are countereffected.

28. The method according to claim 22, wherein the attaching and positioning comprises mounting the at least one gyroscope such that tremors are countereffected in at least one of one, two, and three planar directions.

29. The method according to claim 22, further comprising determining a rotational direction of at least one flywheel in said at least one gyroscope, based upon input from the dynamic characteristics of the patient's tremors and the at least one activity the patient to perform with his/her hand, wrist, and arm which is subject to tremors, such that the patient's tremors are countereffected as a result of the rotational direction of the at least one flywheel in the at least one gyroscope.

30. The method according to claim 22, further comprising determining a rotational direction of at least one flywheel in the at least one gyroscope, based upon input from the dynamic characteristics of the patient's tremors and the at least one activity the patient intends to perform with his/her hand, wrist, and arm which is subject to tremors, such that the patient's hand, wrist, and arm are pulled or panned in a direction opposing the patient's tremors, as a result of the rotational direction of the at least one flywheel in the at least one gyroscope.

31. The method according to claim 22, further comprising one of increasing and decreasing the spin rate of at least one flywheel in the at least one gyroscope according to the dynamic characteristics of the patient's tremors and the at least one activity the patient is to perform with his/her hand, wrist, and arm which is subject to tremors, such that the amount of countereffective force resulting from the at least one gyroscope is increased or decreased.

32. A method for tuning and adjusting a device for stabilizing tremors, the device comprising a rigid splint for receiving a patient's hand, wrist and arm and at least one gyroscope removably and rigidly attached to said splint for countereffecting the tremors, the method comprising:

assessing the dynamic characteristics of the patient's tremors;

assessing at least one activity the patient intends to perform with his/her hand, wrist, and arm which is subject to tremors;

attaching the splint to the patient's hand, wrist, and arm that he/she intends to use for the at least one activity;

attaching the at least one gyroscope to the splint at a position which countereffects the patient's tremors based upon input from dynamic characteristics of the patient's tremors and the at least one activity the patient intends to perform with his/her hand, wrist, and arm which is subject to tremors; and operating the at least one gyroscope to countereffect the patient's tremors while the patient performs the at least one activity with his/her hand, wrist, and arm which is subject to tremors.

33. The method according claim 32, wherein the attaching and positioning comprises mounting the at least one gyroscope to the splint so that the splint and at least one gyroscope are balanced as an entire unit.

34. The method according to claim 32, wherein the attaching and positioning comprises mounting the at least one gyroscope to the splint in an out of balance position to induce at least one of a pulling, tipping, and rolling force in a desired direction.

35. The method according to claim 32, wherein the attaching and positioning comprises orienting the at least one gyroscope such that tremors that at least one of pitch about an x-axis, yaw about a y-axis, and roll about a z-axis are countereffected.

36. The method according to claim 32, wherein the attaching and positioning comprises mounting the at least one gyroscope such that tremors are countereffected in at least one of one, two, and three planar directions.

37. The method according to claim 32, further comprising determining a rotational direction of at least one flywheel in the at least one gyroscope, based upon input from the dynamic characteristics of the patient's tremors and the at least one activity the patient to perform with his/her hand, wrist, and arm which is subject to tremors, such that the patient's tremors are countereffected as a result of the rotational direction of the at least one flywheel in the at least one gyroscope.

38. The method according to claim 32, further comprising determining a rotational direction of at least one flywheel in said at least one gyroscope, based upon input from the dynamic characteristics of the patient's tremors and the at least one activity the patient intends to perform with his/her hand, wrist, and arm which is subject to tremors, such that the patient's hand, wrist, and arm are pulled or panned in a direction opposing the patient's tremors, as a result of the rotational direction of the at least one flywheel in the at least one gyroscope.

* * * * *